(12) United States Patent
Cooke (10) Patent No.: US 11,813,254 B2
(45) Date of Patent: Nov. 14, 2023

(54) COMPOSITIONS AND METHODS FOR REDUCING LAMINITIS OF AN ANIMAL HOOF

(71) Applicant: Equine Podiatry Solutions, LLC., Claxton, GA (US)

(72) Inventor: Derrick Cooke, Brooklet, GA (US)

(73) Assignee: EQUINE PODIATRY SOLUTIONS, LLC., Claxton, GA (US)

( * ) Notice: Subject to any disclaimer, the term of this patent is extended or adjusted under 35 U.S.C. 154(b) by 47 days.

(21) Appl. No.: 17/146,800

(22) Filed: Jan. 12, 2021

(65) Prior Publication Data
US 2021/0213003 A1    Jul. 15, 2021

Related U.S. Application Data

(60) Provisional application No. 62/960,370, filed on Jan. 13, 2020.

(51) Int. Cl.
*A61K 31/444*  (2006.01)
*A61P 19/00*    (2006.01)
*A61K 47/20*    (2006.01)

(52) U.S. Cl.
CPC ............ *A61K 31/444* (2013.01); *A61K 47/20* (2013.01); *A61P 19/00* (2018.01)

(58) Field of Classification Search
CPC .... A61K 31/444; A61K 47/20; A61K 9/0014; A61P 19/00
See application file for complete search history.

(56) References Cited

U.S. PATENT DOCUMENTS

2007/0142317 A1* 6/2007 Warren ................... A61P 17/06
                                                        514/46
2012/0100183 A1* 4/2012 Schlessinger ........... A61P 29/00
                                                        514/772

OTHER PUBLICATIONS

Stover et al (Arch Dermatol Res., 2016, 308:711-721) (Year: 2016).*

* cited by examiner

*Primary Examiner* — Savitha M Rao
(74) *Attorney, Agent, or Firm* — THOMAS | HORSTEMEYER, LLP (57) ABSTRACT

A therapeutic composition for topical delivery of a metalloporphyrin to the hoof region of an equine leg suffering from laminitis is provided. Also provided is a method of reducing the degree of an injury to the hoof of an equine that is the result of laminitis. The method results in a reduced period for recovery and reduces the possibility of euthanasia of the animal.

2 Claims, 5 Drawing Sheets

COMPOSITIONS AND METHODS FOR REDUCING LAMINITIS OF AN ANIMAL HOOF

CROSS-REFERENCE TO RELATED APPLICATIONS

This application claims priority to U.S. Provisional Patent Application Ser. No. 62/960,370 entitled "COMPOSITIONS AND METHODS FOR REDUCING LAMINITIS OF AN ANIMAL HOOF" filed on Jan. 13, 2020, the entirety of which is hereby incorporated by reference.

TECHNICAL FIELD

The present disclosure is generally related to compositions for treating equine laminitis. The present disclosure is also generally related to methods of preparing and using the composition for a reduction in laminitis of an animal hoof.

SUMMARY

One aspect of the disclosure, therefore, encompasses embodiments of a therapeutic composition that can comprise at least one metalloporphyrin, a thickening agent, and a penetrative carrier.

In some of the embodiments of this aspect of the disclosure, the penetrative carrier can be dimethyl sulfoxide.

In some of the embodiments of this aspect of the disclosure, the at least one metalloporphyrin can be manganese (III) meso-tetrakis(N-ethylpyridinium-2-yl) porphyrin chloride.

Another aspect of the disclosure encompasses embodiments of a method of ameliorating the adverse effects of equine laminitis comprising: topically administering to an equine having a laminitis injury an effective amount of a therapeutic composition, wherein the therapeutic composition can comprise at least one metalloporphyrin and a thickening or gelling agent dispersed in a penetrative carrier, wherein the therapeutic composition can be administered to a region of the leg of the equine having the laminitis injury; and continuing to administer the composition until the equine shows a reduction in the degree of injury due to laminitis.

In some of the embodiments of this aspect of the disclosure, the penetrative carrier can be dimethyl sulfoxide.

In some of the embodiments of this aspect of the disclosure, the at least one metalloporphyrin can be manganese (III) meso-tetrakis(N-ethylpyridinium-2-yl) porphyrin chloride.

In some of the embodiments of this aspect of the disclosure, the therapeutic composition consists of manganese(III) meso-tetrakis(N-ethylpyridinium-2-yl) porphyrin chloride, dimethyl sulfoxide, and a thickening agent.

BACKGROUND

Equine laminitis, which is sometimes referred to as foundering, is a common disorder that has been recognized and described in even the earliest books of veterinary medicine. Despite the gathering of voluminous information over a period exceeding 300 years, equine laminitis remains incompletely understood. While it is possible that an afflicted animal can spontaneously recover without intervention treatment, during the course of the disease there is substantial pain, recumbency, hoof wall deformation and even sloughing of the hooves. Symptoms include: a bounding digital pulse, warm feet, an abnormal gait, a shifting of weight, or a combination of some or all of these. If the animal does not recover, after the onset of lameness, the laminae deteriorate, the animal's feet are extremely painful, and the coffin bone becomes displaced. Destruction of the animal is then the only humane course of action.

Since the condition appears to be a function of a loss of circulation in the hoof area, many current treatments have been directed to increasing the blood supply to and circulation within the hoof and adjacent tissues. Several different vasodilators have been used to treat this disorder. Many of them involve the use of nitroglycerin, which has been applied transdermally. Other methods use orally administered isoxsuprine, also a known vasodilator. Use of anticoagulants, such as heparin, aspirin and trental (pentoxifylline) is known. All current therapies suffer from one or more drawbacks, including difficulty in the mode of administration of the active drug, lack of effectiveness, lack of compliance and lack of simplicity in the proposed treatment regimen. However, a strong need remains for an effective treatment of equine laminitis.

BRIEF DESCRIPTION OF THE DRAWINGS

Further aspects of the present disclosure will be more readily appreciated upon review of the detailed description of its various embodiments, described below, when taken in conjunction with the accompanying drawings.

DETAILED DESCRIPTION

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, dimensions, frequency ranges, applications, or the like, as such can vary. It is also to be understood that the terminology used herein is for purposes of describing particular embodiments only and is not intended to be limiting. It is also possible in the present disclosure that steps can be executed in different sequence, where this is logically possible. It is also possible that the embodiments of the present disclosure can be applied to additional embodiments involving measurements beyond the examples described herein, which are not intended to be limiting. It is furthermore possible that the embodiments of the present disclosure can be combined or integrated with other measurement techniques beyond the examples described herein, which are not intended to be limiting.

It should be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. Further, documents or references cited in this text, in a Reference List before the claims, or in the text itself; and each of these documents or references ("herein cited references"), as well as each document or reference cited in each of the herein-cited references (including any manufacturer's specifications, instructions, etc.) are hereby expressly incorporated herein by reference.

Prior to describing the various embodiments, the following definitions are provided and should be used unless otherwise indicated.

The term "diagnosed" as used herein, refers to the recognition of a disease by its signs and symptoms (e.g., resistance to conventional therapies), or genetic analysis, pathological analysis, histological analysis, and the like.

The terms "administration of" and "administering" a compound or composition as used herein refers to providing a compound of the disclosure or a prodrug of a compound of the disclosure to the individual in need of treatment.

The terms "treat" or "treatment" as used herein refer to therapeutic treatment, where the object is to prevent or slow down (lessen) an undesired disorder.

The term "treating" as used herein refers to reversing, alleviating, or inhibiting the progress of an injury, to which such term applies.

The term "composition" as used herein refers to a product comprising the specified ingredients in the specified amounts, as well as any product which results, directly or indirectly, from combination of the specified ingredients in the specified amounts. Such a term in relation to a pharmaceutical composition is intended to encompass a product comprising the active ingredient(s), and the inert ingredient(s) that make up the carrier, as well as any product which results, directly or indirectly, from combination, complexation, or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a compound of the present disclosure and a pharmaceutically acceptable carrier.

The term "formulation" as used herein refers to a composition that may be a stock solution of the components, or a composition, preferably including a dilutant such as water or other pharmaceutically acceptable carrier that may be available for distribution including to a patient or physician.

The term "therapeutically effective amount" relates to the amount or dose of an active compound of the disclosure or composition comprising the same, that will lead to one or more desired effects, in particular, one or more therapeutic effects or beneficial pharmacokinetic profiles. A therapeutically effective amount of a substance can vary according to factors such as the injury state, and weight of the subject, and the ability of the substance to elicit a desired response in the subject. A dosage regimen may be adjusted to provide the optimum therapeutic response or pharmacokinetic profile. For example, several divided doses may be administered daily or the dose may be proportionally reduced as indicated by the exigencies of the therapeutic situation.

The terms "effective amount," "therapeutically-effective amount," and "therapeutically effective dose" as used herein refer to the amount of a compound, material, or composition comprising a compound or composition of the present disclosure, and which is effective for producing a desired therapeutic effect, biological or medicinal response in a tissue system or animal that is being sought by a researcher or veterinarian, which includes alleviation of the symptoms of the disorder being treated or a reduction in a side-effect due to an administered pharmaceutical agent.

The term "therapeutic effect" as used herein refers to an effect of a composition of the disclosure, in particular a formulation or dosage form, or method disclosed herein. A therapeutic effect may be a sustained therapeutic effect that correlates with a continuous concentration of a compound of the disclosure over a dosing period, in particular a sustained dosing period. A therapeutic effect may be a statistically significant effect in terms of statistical analysis of an effect of a compound of the disclosure versus the effects without the compound.

The term "pharmaceutically acceptable carrier, excipient, or vehicle" as used herein refers to a medium which does not interfere with the effectiveness or activity of an active ingredient and which is not toxic to the hosts to which it is administered. A carrier, excipient, or vehicle includes diluents, binders, adhesives, lubricants, disintegrates, bulking agents, wetting or emulsifying agents, pH buffering agents, and miscellaneous materials such as absorbents that may be needed in order to prepare a particular composition. The use of such media and agents for an active substance is well known in the art.

The term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of the disclosure may also include "pharmaceutically acceptable salt(s)". By pharmaceutically acceptable salts is meant those salts which are suitable for use in contact with the tissues of a subject or patient without undue toxicity, irritation, allergic response and the like, and are commensurate with a reasonable benefit/risk ratio. Pharmaceutically acceptable salts are described for example, in S. M, Berge, at al., J. Pharmaceutical Sciences, 1977, 66:1. Suitable salts include salts that may be formed where acidic protons in the compounds are capable of reacting with inorganic or organic bases. Suitable salts include acid addition salts formed with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). When there are two acidic groups present, a pharmaceutically acceptable salt may be a mono-acid-mono-salt or a di-salt; and similarly where there are more than two acidic groups present, some or all of such groups can be salified.

The term "laminitis" as used herein refers to a potentially devastating condition that can strike any hoofed animal but is primarily known to affect equine. Generally speaking, laminitis is a syndrome involving the sensitive laminae of the hoof. The lamina is a layer of loose connective tissue attaching the distal phalanx to the hoof wall by means of collagen.

Laminitis is an inflammation of the pedal laminae that form the supportive bond between the hoof and the third phalanx. The cause of laminitis is varied. It is a complex, multi-systemic disease affecting the digestive, cardiovascular, hemic, renal, endocrine, musculoskeletal, integumentary, and immune systems and characterized by multi-systemic aberrations that ultimately result in reduced capillary perfusion, ischemia, and necrosis of the laminae. These results are accompanied by pain and loss of supportive function.

Acute laminitis is described as comprising the events leading up to and the onset of lameness but can progress to the chronic stage. The chronic stage ensues after persistent lameness (greater than 48 hours), or when the distal phalanx deviates detectably. Chronic laminitis is a consequence of some degree of loss of integrity of the supporting digital laminae. Typically, the horse assumes a recumbent position in which most of the weight is placed on the hind limbs and little weight-bearing pressure is exerted on the forelimbs.

The syndrome can proceed through several stages, beginning with little or no visible signs of the disease, though lamellar damage may have already occurred at this point. Once begun, if unchecked, the condition can advance to a chronic stage, which can involve detachment of the lamina from the hoof and palmar rotation or even distal displacement of the bone. At the chronic stage, a horse can be left with continuous mild or severe pain which can last indefinitely. It is generally held that the laminitis syndrome is responsible for the permanent debilitation of countless horses every year, affecting all breeds around the world. Laminitis is the second leading cause of death of horses world-wide after colic.

In the healthy horse hoof, the desmosimal bonds of the lamina attach the coffin bone to the hoof wall. The secondary epidermal and dermal laminae join at the basement membrane. This is a meshwork of collagen fibers and lamins crosslinked and anchored by hemidesmosomes to basal epithelial cells at the edge of the epidermal laminae. The basement membrane is tethered to tensile collagen fibers of the dermal laminae. They are bound by a variety of extracellular matrix components and transmembrane receptors that are bridges for cell to cell and cell to extracellular matrix interactions. This is where breakdown occurs.

In the acute phase of laminitis, MMP-2, MMP-9, MMP-1, MMP-13 and ADAMTS-4 have been identified as repressing the wnt-signaling in the extracellular matrix (ECM). Swelling caused from inflammatory leukocytes create MMP-9 and physiological reprogramming of basal epithelial cells by elevated expression of ADAMTS-4 are present in the acute phase of laminitis. Depletion of the large extracellular matrix proteoglycan occurs which then adversely affects the fibrous matrix proteins (collagen). Thus, there is suppressed signal transduction in the extracellular matrix to the cells and impaired attachment of basement membrane by a depletion of the hemidesmosomes caused by MMP-1, MMP-2, and MMP-13. The matrix metalloproteinases are digesting the collagen that holds the dermal and epidermal lamina together as well as providing scaffolding for the extracellular matrix. In short, the desmosimal bonds are broken at the basement membrane as a result of enzymes in the extracellular matrix. Inflammation is the engine that moves the hoof capsule up and away from the coffin bone at the dorsal edge.

A horse hoof surrounds the distal phalanx of the 3rd digit (i.e. digit III of the basic quadradactyl limb of equids and of the basic pentadactyl limb of other mammals) evolved into a single weight-bearing digit in each of the four limbs of *Equus* species and which is covered by complex soft tissue and keratinized (cornified) structures. Since a single digit must bear the full proportion of the animal's weight that is borne by that limb, the hoof is of vital importance to the horse.

The hoof is made up by an outer part, the hoof capsule (composed of various cornified specialized structures) and an inner, living part, containing soft tissues and bone. The cornified material of the hoof capsule is different in structure and properties in different parts. Dorsally, it covers, protects and supports P3 (also known as the coffin bone, pedal bone, PIII). It covers and protects specialized soft tissues (tendons, ligaments, fibro-fatty and/or fibrocartilaginous tissues and cartilage). The upper, almost circular limit of the hoof capsule is the coronet (coronary band), having an angle to the ground of roughly similar magnitude in each pair of feet (i.e. fronts and backs). These angles may differ slightly from one horse to another, but not markedly. The walls originate from the coronet band. Walls are longer in the dorsal portion of the hoof (toe), intermediate in length in the lateral portion (quarter) and very short in palmar/plantar portion (heel). Heels are separated by an elastic resilient structure named the 'frog'. In the palmar/plantar part of the foot, above the heels and the frog, there are two oval bulges named the 'bulbs'.

Just below the coronet, the walls are covered for about an inch by a cornified, opaque 'periople' material. In the palmar/plantar part of the hoof, the periople is thicker and more rubbery over the heels, and it merges with frog material. Not all horses have the same amount of periople. Dry feet tend to lack this substance, which can be substituted with a hoof dressing. The third phalanx (coffin bone; pedal bone; P3;) is completely (or almost completely) covered by the hoof capsule. It has a crescent shape and a lower cup-like concavity. Its external surface mirrors the wall's shape. The corium, a dermo-epidermal, highly vascularized layer between the wall and the coffin bone, has a parallel, laminar shape, and is named the laminae. Laminar connection has a key role in the strength and the health of the hoof. Beneath the rear part of the sole, there is the digital cushion, which separates the frog and the bulb from underlying tendons, joints and bones, providing cushioning protection. In foals and yearlings, the digital cushion is composed of fibro-fatty, soft tissue. In the adult horse, it hardens into a fibrocartilaginous tissue when sufficient, consistent concussion stimulates the back of the hoof. Normal transformation of the digital cushion into fibrocartilagineous tissue is now considered a key goal, both for prevention of, and for rehabilitation of recovering cases of navicular syndrome. The flexor tendon lays deeper, just along the posterior surface of the small pastern bone (PII) and navicular bone, and it connects with the posterior surface of P3; the navicular functions as a fulcrum point over a pulley.

There are several disorders and injuries that can affect the equine hoof. Laminitis and navicular disease are two of the most serious. Thrush and white line disease, common bacterial infections, can become serious if left untreated. Quittor, an infection of the lower leg that can travel under the hoof, is also sometimes seen, although most commonly in draft horses. Quarter cracks are vertical splits in a hoof wall, most commonly seen on the inside of the front hooves or the outside of the hind hooves. They can result from poor shoeing and management practices, natural hoof conformation, or injuries to the leg and hoof.

The bones of the hoof are suspended within the axial hooves of ungulates by layers of modified skin cells, known as laminae or lamellae, which act as shock absorbers during locomotion. In horses, there are about 550-600 pairs of primary epidermal laminae, each with 150-200 secondary laminae projection from their surface. These interdigitate with equivalent structures on the surface of the coffin bone (PIII, P3, the third phalanx, pedal bone, or distal phalanx), known as dermal laminae. The secondary laminae contain basal cells which attach via hemidesmosomes to the basement membrane. The basement membrane is then attached to the coffin bone via the connective tissue of the dermis.]

Laminitis literally means inflammation of the laminae, and while it remains controversial whether this is the primary mechanism of disease, evidence of inflammation occurs very early in most instances of the disease. A severe inflammatory event is thought to damage the basal epithelial cells, resulting in dysfunction of the hemidesmosomes and subsequent reduction in adherence between the epithelial cells and the basement membrane. Normal forces placed on the hoof are then strong enough to tear the remaining laminae, resulting in a failure of the interdigitation of the epidermal and dermal laminae between the hoof wall and the coffin bone. When severe enough, this results in displacement of the coffin bone within the hoof capsule. Most cases of laminitis occur in both front feet, but laminitis may be seen in all four feet, both hind feet, and in cases of support limb laminitis in a single foot.

Matrix Metalloproteinases:

The mechanism of laminitis has been linked with matrix metalloproteinases (MMPs) (see, for example, Kyaw-Tanner et al., (2008) Equine Vet. J. 40:482-487). Metalloproteinases are enzymes that can degrade collagen, growth factors, and cytokines to remodel the extracellular matrix of tissues. To prevent tissue damage, they are regulated by tissue inhibitors of metalloproteinases (TIMPs). In cases of laminitis, an underlying cause is thought to cause an imbalance of MMPs and TIMPs, favoring MMPs, so that they may cleave substances within the extracellular matrix and therefore break down the basement membrane. Since the basement membrane is the main link between the hoof wall and the connective tissue of P3, it is thought that its destruction results in their separation. While MMP-2 and MMP-9 are the primary enzymes thought to be linked to laminitis, there have been indications that other such enzymes are also associated with this injury. For example, MMP-1 digests collagen types I, II, and III, MMP-2 digests collagen type IV, MMP-9 digests collagen types IV and V as well as other extracellular matrix proteins resulting in interfering with cell signaling, MMP-13 digests collagen types I, II, and III, as well as containing a conserved forkhead response element (FHRE) sequence for phospho-FoxO3a cell signaling resulting in apoptotic cell death, and ADAMTS-4 cleaves all the chondroitin sulfate hyaluronan-bonding proteoglycans (CSPGs) including aggrecan, brevican, neuronal, and versican.

While enzymatic and inflammation are considered causes of the onset of laminitis, other potential causes are vascular abnormalities, and physical trauma. Thus, in the latter case, concussion is thought to directly damage lamellae, and increased weight-bearing is thought to decrease blood supply to the foot.

Normally, the front of the third phalanx is parallel to the hoof wall and its lower surface should be roughly parallel to the ground surface. A single severe laminitic episode or repeated, less severe episodes can, depending upon the degree of separation of dermal and epidermal laminae, lead to either rotation or sinking of the pedal bone, both of which result in anatomical changes in the position of the coffin bone with visible separation of the laminae, colloquially known as founder. Rotation and distal displacement may occur in the same horse. Both forms of displacement may lead to the coffin bone penetrating the sole. Penetration of the sole is not inherently fatal; many horses have been returned to service by aggressive treatment by a veterinarian and farrier, but the treatment is time-consuming, difficult and expensive.

Rotation is the most common form of displacement, and, in this case, the tip of the coffin bone rotates downward. The degree of rotation may be influenced by the severity of the initial attack and the time of initiation and aggressiveness of treatment.

Sinking is less common and much more severe. It results when a significant failure of the interdigitation between the sensitive and insensitive laminae around a significant portion of the hoof occurs. The destruction of the sensitive laminae results in the hoof wall becoming separated from the rest of the hoof, so that it drops within the hoof capsule. Sinking may be symmetrical, i.e., the entire bone moves distally, or asymmetric, where the lateral or medial aspect of the bone displaces distally. Pus may leak out at the white line or at the coronary band. In extreme cases, this event allows the tip to eventually penetrate the sole of the foot. A severe "sinker" usually warrants the gravest prognosis and may, depending upon many factors, including the quality of aftercare, age of the horse, diet and nutrition, skill, and knowledge and ability of the attending veterinarian and farrier(s), lead to treatment failure and euthanasia of the patient.

The laminitis developmental phase is the time between the initial exposure to the causative agent or incident, until the onset of clinical signs, generally lasting 24-60 hours and is the best time to treat a laminitis episode.

Acute phase: The acute phase is the first 72 hours following the initiation of clinical signs. Treatment response during this time determines if the horse will go into the subacute phase or chronic phase. In the subacute phase there is minimal damage to the lamellae. Clinical signs seen in the acute phase resolve, and the horse becomes sound. The horse never shows radiographic changes, and there is no injury to the coffin bone.

In the chronic phase, however, if damage to the lamellae is not controlled early in the process the coffin bone displaces. Other changes may include separation of the dermal and epidermal lamellae, lengthening of the dermal lamellae, and compression of the coronary and solar dermis. If laminitis can continue, long-term changes such as remodeling of the apex and distal border of the coffin bone (so that a "lip" develops) and osteolysis of the coffin bone can occur.

In compensated cases hoof structure will have been altered, including founder rings, wide white lines, and decreased concavity to the sole. Horses will be relatively sound. On radiographs, remodeling of the coffin bone and in cases of rotational displacement, the distal hoof wall will be thicker than that proximally. Venograms will have relatively normal contrast distribution, including to the apex and distal border of the coffin bone, and the coronary band, but "feathering" may be present at the lamellar "scar."

Uncompensated cases will develop a lamellar wedge (pathologic horn), leading to a poor bridge between P3 and the hoof capsule leading to irregular horn growth and chronic lameness, and horses will suffer from laminitis "flares." The dorsal horn will tend to grow outward rather than down, the heels will grow faster than the toe, and the white line will widen, leading to a potential space for packing of debris. The solar dermis is often compressed enough to inhibit growth, leading to a soft, thin sole that may develop seromas. In severe cases where collapse of the suspensory apparatus of P3 has occurred, the solar dermis or the tip of P3 may penetrate the sole. The horse will also be prone to recurrent abscessation within the hoof capsule. Venogram will show "feathering" into the vascular bed beneath the lamellae, and there will be decreased or absent contrast material in the area distal to the apex of the coffin bone.

Early diagnosis is essential to effective treatment. However, early outward signs may be nonspecific. Careful physical examination typically is diagnostic, but radiographs are also very useful. Laminitic horses are generally sore to pressure from hoof testers applied over the toe area. However, there is risk of a false negative if the horse naturally has a thick sole, or if the hoof capsule is about to slough.

Radiographs: Radiographs are an important part of evaluating the laminitic horse. They only allow the practitioner to determine the severity of the episode, which does not always correlate with degree of pain, and to gauge improvement and response to treatment. As shown in Example 1, Several measurements are made to predict severity. Additionally, radiographs also allow the visualization and evaluation of the hoof capsule and can help detect the presence of a lamellar wedge or seromas. The lateral view provides the majority of the information regarding degree of rotation, sole depth, dorsal hoof wall thickness, and vertical deviation. A 65-degree dorsopalmar view is useful in the case of chronic laminitis to evaluate the rim of the coffin bone for pathology.

The term "pharmaceutically acceptable" in reference to an entity or ingredient is one that may be included in the compositions provided herein and that causes no significant adverse toxicological effects in the patient at specified levels, or if levels are not specified, in levels known to be acceptable by those skilled in the art. All ingredients in the compositions described herein are provided at levels that are pharmaceutically acceptable. For clarity, active ingredients may cause one or more side effects and inclusion of the ingredients with a side effect profile that is acceptable from a regulatory perspective for such ingredients would be deemed to be "pharmaceutically acceptable" levels of those ingredients.

The term "topical composition" refers to a material that comprises pharmaceutically acceptable ingredients, including an active ingredient, and is intended for administration to an animal subject and is applied to the surface of the skin, in contrast to materials that are taken orally or via intravenous (subdermal) injection. A topical composition is generally intended to have its intended effect at the site of application and does not result in significant concentrations of active ingredient in the bloodstream or other tissues (as is the case with, for example, transdermal compositions). Topical compositions as provided herein are typically administered for the purpose of alleviation of injury associated with laminitis of an equine hoof.

The instant compositions may also contain relatively small amounts, e.g., less than about 10% (w/w) of one or more auxiliary excipients suitable for topical use including but not limited to pH modifying agents, preservatives, thickening agents, gel-forming agents, emulsifying agents, antioxidants, scent agents, and the like. Compounds suitable for incorporation may be found, e.g., in R. C. Rowe, et al., Handbook of Pharmaceutical Excipients ($4^{th}$ Ed.), Pharmaceutical Press, London, 2003.

The present disclosure encompasses embodiments of a composition comprising at least one metalloporphyrin and a penetrative agent for topical application to an equine hoof for the treatment of laminitis in the hoof. Further provided are methods for the treatment of laminitis in horses suffering therefrom by application of the compositions of the disclosure.

Reactive Oxygen Species (ROS) control the growth of pathogens. The metalloporphyrin effectively reduces the nuclear factor Kappa Beta binding to DNA and suppresses pro-inflammatory cytokines and ROS allowing activation for T-cell factor by protecting B-catenin in DNA binding. Thus, canonical Wnt-signaling pathway can regulate the expression of genes encoding versican and other proteins; therefore, the desmosimal bonds are protected from the identified enzymes and preserve the laminae from damage. Basically, a metalloporphyrin-based superoxide dismutase (SOD) mimics the reactive oxygen species (ROS) protecting the cells from oxidative stress and death.

The superoxide dismutase (SOD) prevents the reactive oxygen species (ROS) from interrupting signaling in the extracellular matrix. The T-cells remain able to function and the immune system remains effective. The desmosimal bonds of the laminae stay intact and strong.

It has now been surprisingly found that a topical application of a metalloporphyrin to the hoof of an animal suffering the acute phase of laminitis results in a rapid recovery from the disease regardless of the cause. By applying the compositions of the disclosure at the early acute phase of laminitis it has been found that horses can recover to full service health whereas without this treatment the prognosis would be that euthanasia was the only means of preventing prolonged and painful deterioration of the affected hooves.

The compositions of the disclosure, therefore, are comprised of a metalloporphyrin dissolved in a penetrative solvent, and further comprises a thickening agent that allows the active ingredient to remain on the treated area of the hoof for sufficient time for the active agent to penetrate into the underlying tissues. While not wishing to be limited, advantageously, the compositions of the disclosure comprise at least one metalloporphyrin selected from the group comprising Manganese (III) meso-tetrakis (N,N'-diethylimidazolium-2-yl) porphyrin (AEOL-10150), Manganese (III) meso-tetrakis (N-ethylpyridinium-2-yl) porphyrin, Manganese (III) meso-tetrakis (2-pyridyl) porphyrin, Manganese (III) meso-tetrakis (3-pyridyl) porphyrin, Manganese (III) meso-tetrakis (4-pyridyl) porphyrin, Manganese (III) meso-tetraphenylporphyrin, Manganese (III) meso-tetrakis (N-alkylpyri-dinium-2-yl) porphyrin (AEOL-10112), Manganese (III) meso-tetrakis (N-alkylpyri-dinium-3-yl) porphyrin (AEOL-10113), Manganese (III) meso-tetrakis (N-alkylpri-dinium-4-yl) porphyrin, Manganese 5,10-bis(2-pyridyl)-15, 20-bis(N-methylpyridinium-2-yl) porphyrin, Manganese 5-(2-pyridyl)-10,15,20-tris(N-methylpyridinium-2-yl) porphyrin, Manganese 5,10,15,20-tetrakis(2,3,5,6-tetrafluoro-N,N,N-trimethylanilinium-4-yl)porphyrin, Manganese (II) B-octabromo-meso-tetrakis(N-methylpyridinium-3-yl)porphyrin, Manganese (II) B-octabromo-meso-tetrakis(N-methylperidinium-4-yl)porphyrin, Manganese (III) B-(mono-tetra) chloro-meso-tetrakis(N-ethylpyridinium-2-yl)porphyrin, Manganese (II) B-pentacloro-meso-tetrakis (N-ethylpyridinium-4-yl)porphyrin, Manganese (III) meso-tetrakis (4-sulfonatophenyl)porphyrin, Manganese (III) meso-tetrakis (4-carboxylatophenyl)porphyrin, Manganese (III) B-octabromo-meso-tetrakis(4-sulfonatophenyl)porphyrin, Manganese (III) meso-tetrakis (2,6-dichlorvos-3-sulfonatophenyl)porphyrin, MnhemaoP(–). Hematoporphyrin IX, Iron (III) meso-tetrakis (4-carboxylatophenyl) porphyrin, Manganese (III) meso-tetrakis (N-methoxyethylpyridinium-2-yl)porphyrin, Manganese (III) meso-tetrakis [N,N'-di(2-methoxyehyl)imidazilium-2-yl]porphyrin, Manganese (III) tetrakis [N-methyl-N'-methoxethyl)imidazolium-2-yl)porphyrin. Most advantageously, at least one of the metalloporphyrins is manganese (III) meso-tetrakis(N-ethylpyridinium-2-yl) porphyrin chloride (alternatively designated BMX-010 or AEOL-10113) having the formula:

The concentration of the metalloporphyrin(s) in the carrier can be, but is not limited to, between about 0.001% and 20% wt %, between about 0.001% and 10% wt %, between about 0.01% and 20% wt %, between about 0.01% and 10% wt %, between about 0.1% and 20% wt %, between about 0.1% and 10% wt %, between about 0.001% and 5% wt %, between about 0.01% and 5% wt %, between about 0.1% and 5% wt %, between about 0.001% and 1% wt %, between about 0.01% and 1% wt %, between about 0.1% and 1% wt %.

The topical pharmaceutical compositions of the disclosure comprise a penetration enhancer. The term "penetration enhancer" as used herein refers to a compound that enhances the penetration of a therapeutic compound through the skin of an animal such as a horse to deliver the therapeutic compound to an underlying tissue desired to be treated.

Penetration enhancers that can be advantageously used in the compositions and methods of the disclosure include, but are not limited to, fatty acid esters, fatty alcohols, pyrrolidones, sulfoxides, alcohols, diols and polyols, and mixtures thereof. For example, but not intended to be limiting, fatty acid esters include glycerol monolaurate, glycerol monooleate, glycerol monolinoleate, isopropyl isostearate, isopropyl palmitate, isopropyl myristate, diethylsebacate, sorbitan monopalmitate, sorbitan oleate, sorbitan dilaurate, sorbitan trioleate, propylene glycol monolaurate and sucrose monolaurate, and mixtures thereof. Fatty alcohols can include such as cetyl alcohol, stearyl alcohol, decanol, tridecanol, lauryl alcohol, linolenyl alcohol and oleyl alcohol, and mixtures thereof. Pyrrolidones can include such as N-methyl pyrrolidone, 2-pyrrolidone and N-cyclohexyl-2-pyrrolidone, and mixtures thereof. Sulfoxides can include such as dimethyl sulfoxide and decylmethyl sulfoxide, and mixtures thereof. Alcohols can include such as lower ($C_1$-$C_6$) alcohols and diethylene glycol monoethyl ether, and mixtures thereof. Diols include, but are not limited to, 1,2-hexanediol, butylene glycol, diethylene glycol, dipropylene glycol, ethyl hexanediol, ethylene glycol, hexylene glycol, pentylene glycol, propylene glycol, propylene glycol monolaurate, tetraethylene glycol, triethylene glycol, tripropylene glycol, polyethylene glycol and polypropylene glycol, and mixtures thereof. Polyols include, but are not limited to, butanetriol, glycerol and 1,2,6-hexanetriol, and mixtures thereof.

One advantageous penetration enhancer for use in the compositions of the disclosure is dimethyl sulfoxide (DMSO). While not desirable as a penetrant for application to the skin of a human, DMSO has been found to be useful for the delivery of a metalloporphyrin to the tissues of an equine. To extend the application or treatment time, it has been found advantageous to include a thickening agent that retains the therapeutic composition at the point of application.

Suitably, the penetration enhancer is present in the composition in an amount from about 0.5% to about 40% by weight, such as from about 1% to about 20% by weight or from about 5% to about 15% by weight, based on the total weight of the composition.

Suitably, the penetration enhancer is present in the composition in an amount from about 0.5% to about 40% by weight, such as from about 1% to about 20% by weight or from about 5% to about 15% by weight, based on the total weight of the composition.

The present topical pharmaceutical compositions may further comprise a gelling agent. In an embodiment, the gelling agent is a mixture of two or more gelling agents. Gelling agents which may be used in the topical compositions include conventional gelling agents well known for their gelling properties, such as, for example, cellulose ethers such as hydroxypropyl cellulose, hydroxypropyl methylcellulose, carboxymethyl cellulose, sodium carboxymethyl cellulose, hydroxyethyl cellulose, and the like; vinyl alcohols; vinyl pyrrolidones; natural gums such as karaya gum, locust bean gum, guar gum, gelan gum, xanthan gum, gum arabic, tragacanth gum, carrageenan, pectin, agar, alginic acid, sodium alginate and the like. Other gelling agents can include polyoxyethylene-polyoxypropylene copolymers (poloxamers). Suitable gelling agents can include those absent free carboxyl groups such as, for instance, hydroxypropylcellulose, hydroxypropylmethylcellulose, hydroxyethylcellulose, methylcellulose, organo/cold water soluble cellulose, hydroxyethylmethylcellulose, ethylcellulose, ethyl(hydroxyethyl)cellulose.

Advantageously, the gelling agent can present in the composition in an amount from about 0.1% to about 2% by weight, based on the total weight of the composition. In one embodiment, the gelling agent is present in the composition in an amount from about 0.2% to about 1% by weight, based on the total weight of the composition.

The pharmaceutically acceptable metalloporphyrins for use in the compositions and methods of the disclosure are suitable for application to the lower leg or hoof of an equine for the treatment of a laminitis injury thereof. The formulations of the disclosure can include any of the various known excipients which may be applied topically and which will permit even spreading of the active ingredient over the affected area, rapid drying, and/or increased penetration, and especially to retain the therapeutic composition on the treated area rather than, for example, having dimethyl sulfoxide, a volatile and low viscosity liquid, flow or evaporate away from the treated area of the equine leg. Examples of suitable formulations include solutions, milks, creams, ointments, gels, lotions, sprays, aerosols, foam, or suspensions.

Dosage

Therapeutic efficacy and toxicity of compounds, compositions and methods of the disclosure may be determined by standard pharmaceutical procedures in cell cultures or with experimental animals such as by calculating a statistical parameter such as the $ED_{50}$ (the dose that is therapeutically effective in 50% of the population) or $LD_{50}$ (the dose lethal to 50% of the population) statistics. The therapeutic index is the dose ratio of therapeutic to toxic effects and it can be expressed as the $ED_{50}/LD_{50}$ ratio. Pharmaceutical compositions which exhibit large therapeutic indices are preferred. By way of example, one or more of the therapeutic effects can be demonstrated in a subject or disease model by the screening methods of the disclosure.

The disclosure provides dosage forms, formulations, and methods that provide advantages and/or beneficial pharmacokinetic profiles, more particularly sustained pharmacokinetic profiles. A compound of the disclosure can be utilized in dosage forms in pure or substantially pure form, in the form of its pharmaceutically acceptable salts, and also in other forms including anhydrous or hydrated forms.

A beneficial pharmacokinetic profile may be obtained by administering a formulation or dosage form suitable for once, twice a day, or three times a day, or more administration comprising one or more compound of the disclosure present in an amount sufficient to provide the required concentration or dose of the compound to an environment of use to treat a disease disclosed herein, in particular a cancer.

Embodiments of the disclosure relate to a dosage form comprising one or more compound of the disclosure that can provide peak plasma concentrations of the compound of between about 0.001 to 2 mg/ml, 0001 to 1 mg/ml, 0.0002 to 2 mg/ml, 0.005 to 2 mg/ml, 001 to 2 mg/ml, 0.05 to 2 mg/ml, 0.001 to 0.5 mg/ml, 0.002 to 1 mg/ml, 0.005 to 1 mg/ml, 0.01 to 1 mg/ml, 005 to 1 mg/ml, or 0.1 to 1 mg/ml. The disclosure also provides a formulation or dosage form comprising one or more compound of the disclosure that provides an elimination $t_{1/2}$ of 0.5 to 20 h, 0.5 to 15 h, 0.5 to 10 h, 0.5 to 6 h, 1 to 20 h, 1 to 15 h, 1 to 10 h, or 1 to 6 h.

A subject may be treated with a compound of the disclosure or composition or unit dosage thereof on substantially any desired schedule. They may be administered one or more times per day, in particular 1 or 2 times per day, once per week, once a month or continuously. However, a subject may be treated less frequently, such as every other day or once a week, or more frequently. A compound or composition may be administered to a subject for about or at least about 24 hours, 2 days, 3 days, 1 week, 2 weeks to 4 weeks, 2 weeks to 6 weeks, 2 weeks to 8 weeks, 2 weeks to 10 weeks, 2 weeks to 12 weeks, 2 weeks to 14 weeks, 2 weeks to 16 weeks, 2 weeks to 6 months, 2 weeks to 12 months, 2 weeks to 18 months, 2 weeks to 24 months, or for more than 24 months, periodically or continuously.

A beneficial pharmacokinetic profile can be obtained by the administration of a formulation or dosage form suitable for once, twice, or three times a day administration, preferably twice a day administration comprising one or more compound of the disclosure present in an amount sufficient to provide the requited dose of the compound. The required dose of a compound of the disclosure administered once twice, three times or more daily is about 0.01 to 3000 mg/kg, 0.01 to 2000 mg/kg, 0.5 to 2000 mg/kg, about 0.5 to 1000 mg/kg, 0.1 to 1000 mg/kg, 0.1 to 500 mg/kg, 0.1 to 400 mg/kg, 0.1 to 300 mg/kg, 0.1 to 200 mg/kg, 0.1 to 100 mg/kg, 0.1 to 50 mg/kg, 0.1 to 20 mg/kg, 0.1 to 10 mg/kg, 0.1 to 6 mg/kg, 0.1 to 5 mg/kg, 0.1 to 3 mg/kg, 0.1 to 2 mg/kg, 0.1 to 1 mg/kg, 1 to 1000 mg/kg, 1 to 500 mg/kg, 1 to 400 mg/kg, 1 to 300 mg/kg, 1 to 200 mg/kg, 1 to 100 mg/kg, 1 to 50 mg/kg, 1 to 20 mg/kg, 1 to 10 mg/kg, 1 to 6 mg/kg, 1 to 5 mg/kg, or 1 to 3 mg/kg, or 1 to 2.5 mg/kg, or less than or about 10 mg/kg, 5 mg/kg, 2.5 mg/kg, 1 mg/kg, or 0.5 mg/kg twice daily or less Certain dosage forms and formulations may minimize the variation between peak and trough plasma and/or brain levels of compounds of the disclosure and in particular provide a sustained therapeutically effective amount of the compounds.

The disclosure also contemplates a formulation or dosage form comprising amounts of one or more compound of the disclosure that results in therapeutically effective amounts of the compound over a dosing period, in particular a 24 h dosing period. The therapeutically effective amounts of a compound of the disclosure are between about 0.1 to 1000 mg/kg, 0.1 to 500 mg/kg, 0.1 to 400 mg/kg, 0.1 to 300 mg/kg, 0.1 to 200 mg/kg, 0.1 to 100 mg/kg, 0.1 to 75 mg/kg, 0.1 to 50 mg/kg, 0.1 to 25 mg/kg, 0.1 to 20 mg/kg, 0.1 to 15 mg/kg, 0.1 to 10 mg/kg, 0.1 to 9 mg/kg, 0.1 to 8 mg/kg, 0.1 to 7 mg/kg, 0.1 to 6 mg/kg, 0.1 to 5 mg/kg, 0.1 to 4 mg/kg, 0.1 to 3 mg/kg, 0.1 to 2 mg/kg, or 0.1 to 1 mg/kg.

A medicament or treatment of the disclosure may comprise a unit dosage of at least one compound of the disclosure to provide therapeutic effects. A "unit dosage" or "dosage unit" refers to a unitary, i.e. a single dose, which is capable of being administered to a patient, and which may be readily handled and packed, remaining as a physically and chemically stable unit dose comprising either the active agents as such or a mixture with one or more solid or liquid pharmaceutical excipients, carriers, or vehicles.

A compound of the disclosure of the disclosure may be formulated into a pharmaceutical composition for administration to a subject by appropriate methods known in the art. Pharmaceutical compositions of the present disclosure or fractions thereof comprise suitable pharmaceutically acceptable carriers, excipients, and vehicles selected based on the intended form of administration, and consistent with conventional pharmaceutical practices. Suitable pharmaceutical carriers, excipients, and vehicles are described in the standard text, Remington: The Science and Practice of Pharmacy (21.sup.st Edition. 2005, University of the Sciences in Philadelphia (Editor), Mack Publishing Company), and in The United States Pharmacopeia: The National Formulary (USP 24 NF19) published in 1999.

One aspect of the disclosure, therefore, encompasses embodiments of a method of ameliorating the adverse effects of equine laminitis comprising: topically administering to an equine having a laminitis injury an effective amount of a therapeutic composition, wherein the therapeutic composition can comprise at least one metalloporphyrin and a thickening or gelling agent dispersed in a penetrative carrier, wherein the therapeutic composition can be administered to a region of the leg of the equine having the laminitis injury; and continuing to administer the composition until the equine shows a reduction in the degree of injury due to laminitis.

In some of the embodiments of this aspect of the disclosure, the at least one metalloporphyrin can be selected from the group consisting of: manganese(III) meso-tetrakis(N-ethylpyridinium-2-yl) porphyrin chloride (BMX-010 or AEOL-10113), Manganese (III) meso-tetrakis (N,N'-diethylimidazolium-2-yl) porphyrin (AEOL-10150), Manganese (III) meso-tetrakis (N-ethylpyridinium-2-yl) porphyrin, Manganese (III) meso-tetrakis (2-pyridyl) porphyrin, Manganese (III) meso-tetrakis (3-pyridyl) porphyrin, Manganese (III) meso-tetrakis (4-pyridyl) porphyrin, Manganese (III) meso-tetraphenylporphyrin, Manganese (III) meso-tetrakis (N-alkylpyri-dinium-2-yl) porphyrin (AEOL-10112), Manganese (III) meso-tetrakis (N-alkylpyri-dinium-3-yl) porphyrin (AEOL-10113), Manganese (III) meso-tetrakis (N-alkylpri-dinium-4-yl) porphyrin, Manganese 5,10-bis(2-pyridyl)-15,20-bis(N-methylpyridinium-2-yl) porphyrin, Manganese 5-(2-pyridyl)-10,15,20-tris(N-methylpyridinium-2-yl) porphyrin, Manganese 5,10,15,20-tetrakis(2,3,5,6-tetrafluoro-N,N,N-trimethylanilinium-4-yl)porphyrin, Manganese (II) B-octabromo-meso-tetrakis(N-methyllpyridiniium-3-yl)porphyrin, Manganese (II) B-octabromo-meso-tetrakis(N-methylperidinium-4-yl)porphyrin, Manganese (III) B-(mono-tetra) chloro-meso-tetrakis(N-ethylpyridinium-2-yl)porphyrin, Manganese (II) B-pentacloro-meso-tetrakis(N-ethylpyridinium-4-yl)porphyrin, Manganese (III) meso-tetrakis (4-sulfonatophenyl) porphyrin, Manganese (III) meso-tetrakis (4-carboxylatophenyl)porphyrin, Manganese (III) B-octabromo-meso-tetrakis(4-sulfonatophenyl)porphyrin, Manganese (III) meso-tetrakis (2,6-dichlorvos-3-sulfonatophenyl)porphyrin, MnhemaoP(−). Hematoporphyrin IX, Iron (III) meso-tetrakis (4-carboxylatophenyl)porphyrin, Manganese (III) meso-tetrakis (N-methoxyethylpyridinium-2-yl)porphyrin, Manganese (III) meso-tetrakis [N,N'-di(2-methoxyehyl) imidazilium-2-yl]porphyrin, and Manganese (III) tetrakis [N-methyl-N'-methoxethyl)imidazolium-2-yl)porphyrin.

In some of the embodiments of this aspect of the disclosure, the penetrative carrier can be dimethyl sulfoxide.

In some of the embodiments of this aspect of the disclosure, the at least one metalloporphyrin can be manganese (III) meso-tetrakis(N-ethylpyridinium-2-yl) porphyrin chloride.

In some of the embodiments of this aspect of the disclosure, the therapeutic composition consists of manganese(III) meso-tetrakis(N-ethylpyridinium-2-yl) porphyrin chloride, dimethyl sulfoxide, and a thickening agent.

In some of the embodiments of this aspect of the disclosure, the composition can be applied daily for at least about one week, two weeks, three weeks, or four weeks.

Another aspect of the disclosure encompasses embodiments of a therapeutic composition that can comprise at least one metalloporphyrin, a thickening agent, and a penetrative carrier.

In some of the embodiments of this aspect of the disclosure, the at least one metalloporphyrin can be selected from the group consisting of: manganese(III) meso-tetrakis(N-ethylpyridinium-2-yl) porphyrin chloride (BMX-010 or AEOL-10113), Manganese (III) meso-tetrakis (N,N'-diethylimidazolium-2-yl) porphyrin (AEOL-10150), Manganese (III) meso-tetrakis (N-ethylpyridinium-2-yl) porphyrin, Manganese (III) meso-tetrakis (2-pyridyl) porphyrin, Manganese (III) meso-tetrakis (3-pyridyl) porphyrin, Manganese (III) meso-tetrakis (4-pyridyl) porphyrin, Manganese (III) meso-tetraphenylporphyrin, Manganese (III) meso-tetrakis (N-alkylpyri-dinium-2-yl) porphyrin (AEOL-10112), Manganese (III) meso-tetrakis (N-alkylpyri-dinium-3-yl) porphyrin (AEOL-10113), Manganese (III) meso-tetrakis (N-alkylpri-dinium-4-yl) porphyrin, Manganese 5,10-bis(2-pyridyl)-15,20-bis(N-methylpyridinium-2-yl) porphyrin, Manganese 5-(2-pyridyl)-10,15,20-tris(N-methylpyridinium-2-yl) porphyrin, Manganese 5,10,15,20-tetrakis(2,3,5,6-tetrafluoro-N,N,N-trimethylanilinium-4-yl)porphyrin, Manganese (II) B-octabromo-meso-tetrakis(N-methyllpyridiniium-3-yl)porphyrin, Manganese (II) B-octabromo-meso-tetrakis(N-methyl peridinium-4-yl)porphyrin, Manganese (III) B-(mono-tetra) chloro-meso-tetrakis(N-ethylpyridinium-2-yl)porphyrin, Manganese (II) B-pentacloro-meso-tetrakis(N-ethylpyridinium-4-yl)porphyrin, Manganese (III) meso-tetrakis (4-sulfonatophenyl) porphyrin, Manganese (III) meso-tetrakis (4-carboxylatophenyl)porphyrin, Manganese (III) B-octabromo-meso-tetrakis(4-sulfonatophenyl)porphyrin, Manganese (III) meso-tetrakis (2,6-dichlorvos-3-sulfonatophenyl)porphyrin, MnhemaoP(−). Hematoporphyrin IX, Iron (III) meso-tetrakis (4-carboxylatophenyl)porphyrin, Manganese (III) meso-tetrakis (N-methoxyethylpyridinium-2-yl)porphyrin, Manganese (III) meso-tetrakis [N,N'-di(2-methoxyehyl) imidazilium-2-yl]porphyrin, and Manganese (III) tetrakis [N-methyl-N'-methoxethyl)imidazolium-2-yl)porphyrin.

In some of the embodiments of this aspect of the disclosure, the penetrative carrier can be dimethyl sulfoxide.

In some of the embodiments of this aspect of the disclosure, the at least one metalloporphyrin can be manganese (III) meso-tetrakis(N-ethylpyridinium-2-yl) porphyrin chloride.

While embodiments of the present disclosure are described in connection with the Examples and the corresponding text and figures, there is no intent to limit the disclosure to the embodiments in these descriptions. On the contrary, the intent is to cover all alternatives, modifications, and equivalents included within the spirit and scope of embodiments of the present disclosure.

EXAMPLES

Example 1

Radiographic Measurements

Figure 1:
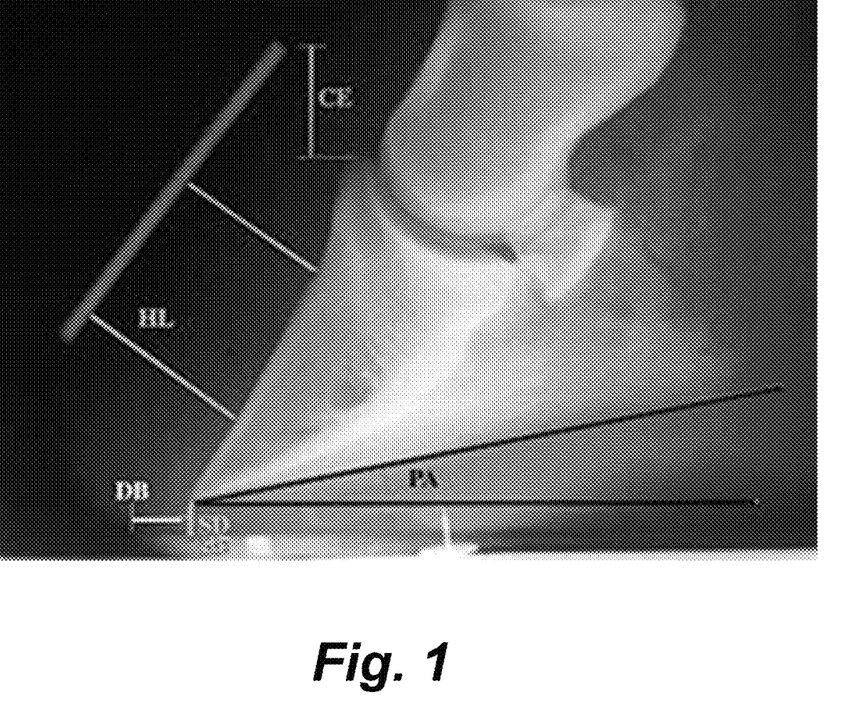
FIG. 1 illustrates the positions of the radiographic measurements including coronary extensor distance (CE), horn: lamellar distance (HL), sole depth (SD), digital breakover (DB), and palmar angle (PA) used to measure the degree of laminitis in a horse's hoof.
Figure 2:
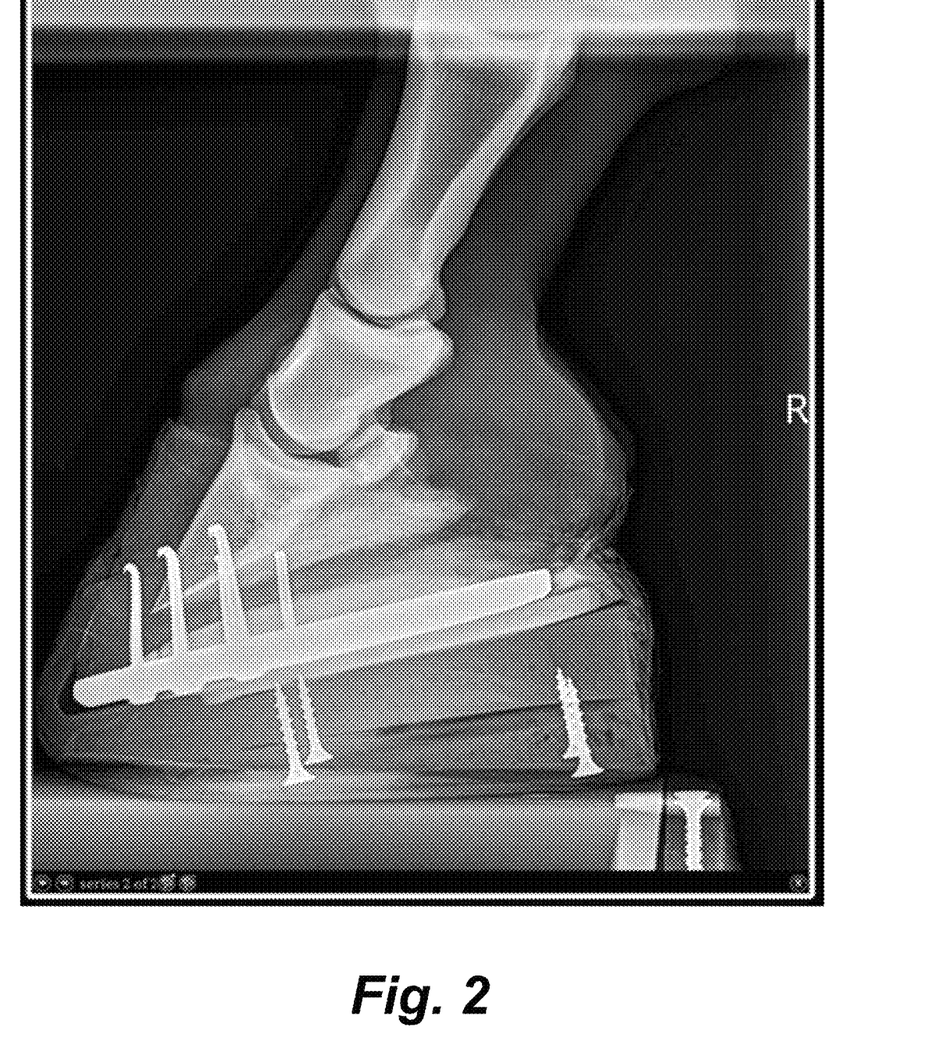
FIG. 2 illustrates a radiograph taken of the right forelimb of the first subject in the study on the first day of treatment 28 hours after entering the feed room and gorging on grain.
Figure 3:
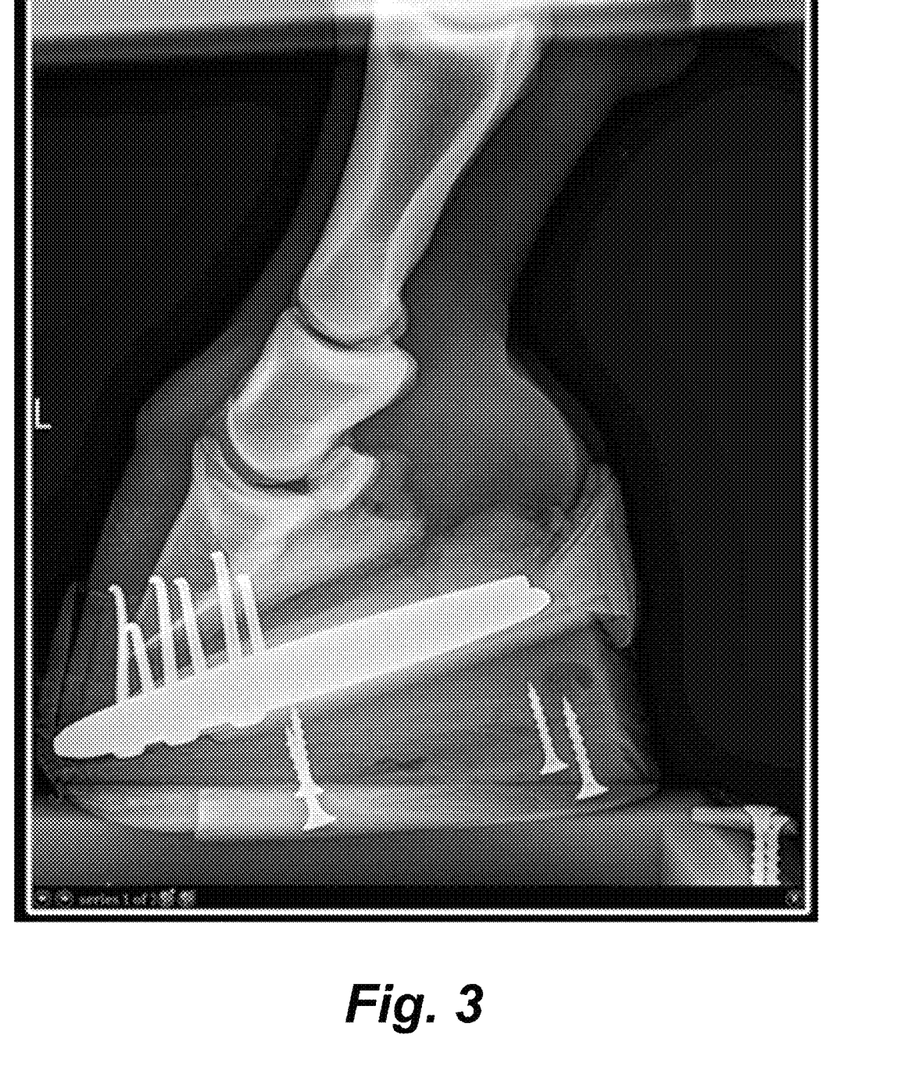
FIG. 3 illustrates a radiograph taken of the left forelimb of the first subject in the study on the first day of treatment 28 hours after entering the feed room and gorging on grain.
Figure 4:
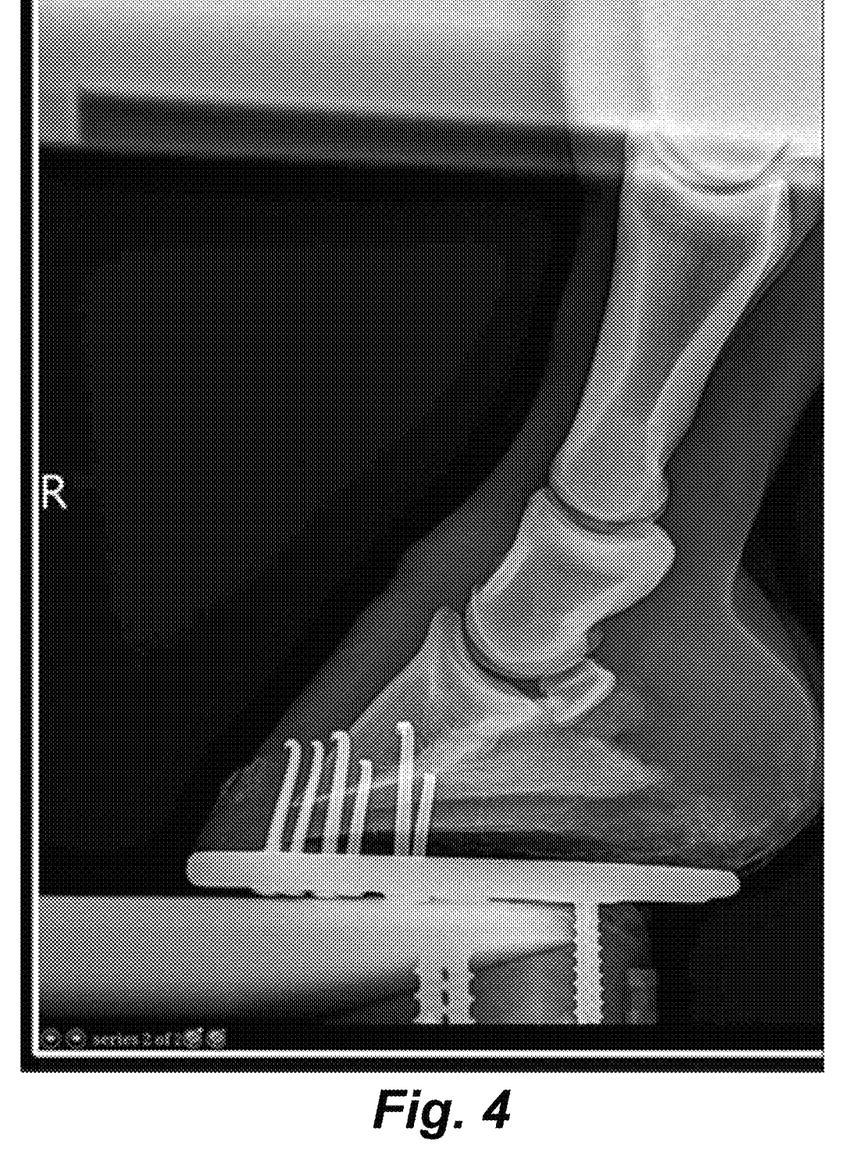
FIG. 4 illustrates a radiograph of the right forelimb of the first subject in the study taken 45 days after treatment. This radiograph shows the horse has no rotation of P-3 nor separation of the dorsal edge of the hoof wall.
Figure 5:
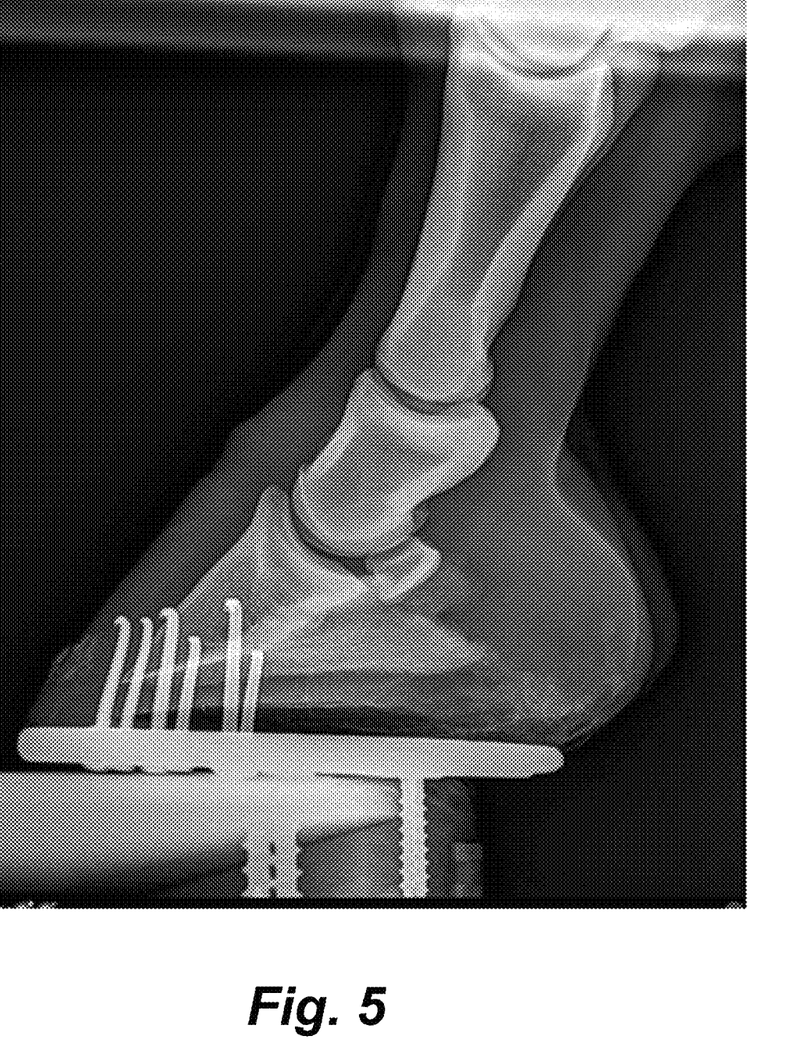
FIG. 5 illustrates a radiograph of the left forelimb of the first subject in the study taken 45 days after treatment. This radiograph shows the horse has no rotation of P-3 nor separation of the dorsal edge of the hoof wall.

As shown in FIG. 1, radiographic measurements include:

Coronary extensor distance (CE): the vertical distance from the level of the proximal coronary band to the extensor process of P3 is used to compare progression of the disease over time. A rapidly increasing CE value can indicate distal displacement (sinking) of the coffin bone, while a more gradual increase in CE can occur with foot collapse. Normal values range from 0-30 mm, with most horses less than 12-15 mm.

Sole depth (SD): distance from the tip of P3 to the ground.

Digital breakover (DB): distance from the tip of P3 to the breakover of the hoof (dorsal toe).

Palmar angle (PA): angle between a line perpendicular to the ground, and a line at the angle of the palmar surface of P3.

Horn:lamellar distance (HL): measurement from the most superficial aspect of the dorsal hoof wall to the face of P3.

Two distances are compared: a proximal measurement made just distal to the extensor process of P3, and a distal measurement made toward the tip of P3. These two values should be similar. In cases of rotation, the distal measurement will be higher than the proximal. In cases of distal displacement, both values will increase, but may remain equal.

Venograms: Venograms can help determine the prognosis for the animal, particularly in horses where the degree of pain does not match the radiographic changes.

Other imaging tools have been used to show mechanical deviations in laminitis cases include computed tomography, as well as MRI, which also provides some physiologic information. Nuclear scintigraphy may also be useful in certain situations. Ultrasonography has been explored as a way to quantify changes in blood flow to the foot.

Example 2

Procedure:

The horse is placed in an 18-degree wedge and administered an intravenous drip of DMSO.

The hairline is shaved 1 inch above the coronary band on all four feet.

A topical solution according to the disclosure is applied every 12 hours to all four feet for a total of 3 days.

Example 3

Formula I

Manganese(III) meso-tetrakis(N-ethylpyridinium-2-yl) porphyrin chloride, 0.01% weight/volume

DMSO

Thickening agent

Example 4

Radiographs (FIGS. 2-5) of a horse that developed the acute phase of laminitis and then was treated days 1, 2, and 3 thereafter showed significant decreasing of the amount of laminitis in this animal. The horse was back under saddle within six weeks and able to compete in rodeo competitions, with the extensive and violent movements required, with no continuing effects of laminitis.

Example 5

A total of 10 horses with indications of acute laminitis were treated with the composition of the disclosure. One horse had binged on grain while the others were overweight and underworked, leading to predisposed metabolic contributors. All 10 were treated within 24 hours of the insult. None of animals showed signs of laminitis damage that would be evidenced by separation of lamina and/or rotation of the coffin bone. All horses returned to full mobility and activity within 2 months.

What is claimed is:

1. A method of ameliorating the adverse effects of equine laminitis comprising: topically administering to an equine having a laminitis injury an effective amount of a therapeutic composition, comprising a manganese metalloporphyrin, a thickening agent, and a penetrative carrier comprising dimethyl sulfoxide, wherein in the manganese metalloporphyrin is manganese(III) meso-tetrakis(N-ethylpyridinium-2-yl) porphyrin chloride.

2. The method of claim 1, wherein the therapeutic composition is applied daily for at least about one week, two weeks, three weeks, or four weeks.

* * * * *